United States Patent [19]

Larson

[11] 4,077,227

[45] Mar. 7, 1978

[54] METHOD OF FREEZING LIQUID MATERIAL IN WHICH AGGLOMERATION IS INHIBITED

[75] Inventor: E. Virgil Larson, St. Paul, Minn.

[73] Assignee: Regents of the University of Minnesota, Minneapolis, Minn.

[21] Appl. No.: 741,304

[22] Filed: Nov. 12, 1976

[51] Int. Cl.² ............................................. F25C 1/00
[52] U.S. Cl. .................................... 62/74; 21/54 R; 21/102 R; 239/3; 361/228
[58] Field of Search ................... 62/74, 347; 21/54 R, 21/102 R; 426/237; 239/3, 15; 361/228

[56] References Cited

U.S. PATENT DOCUMENTS

| | | | |
|---|---|---|---|
| 2,809,128 | 10/1957 | Miller | 239/3 X |
| 2,875,588 | 3/1959 | Berger | 62/74 |
| 3,024,117 | 3/1962 | Barlow | 62/74 X |
| 3,049,092 | 8/1962 | Sedlacsik | 239/3 X |
| 3,162,019 | 12/1964 | Porter et al. | 62/74 X |
| 3,335,322 | 8/1967 | Epstein et al. | 361/228 X |
| 3,927,877 | 12/1975 | Terajima | 271/DIG. 3 |
| 4,004,733 | 1/1977 | Law | 239/3 |

Primary Examiner—William E. Wayner
Assistant Examiner—William E. Tapolcai, Jr.
Attorney, Agent, or Firm—Stuart R. Peterson

[57] ABSTRACT

The liquid material to be frozen is separated into successive drops, each of which is subjected to an electric field of sufficient strength so as to induce on each drop an electric charge, the charges all being of the same polarity. The charged drops are sequentially directed at a controlled rate onto the surface of a cryogenic liquid where they momentarily float while being changed to a solid frozen state. During this interval the electric charges, being of like polarity, produce repulsive forces in accordance with Coulomb's Law which keep the drops apart so that they freeze and sink as individual pellets. The lack of agglomeration enables the pellets to be more rapidly and uniformly frozen and more rapidly and uniformly thawed for use at a later time. In this way, substances vulnerable to deterioration can be preserved for prolonged periods.

14 Claims, 1 Drawing Figure

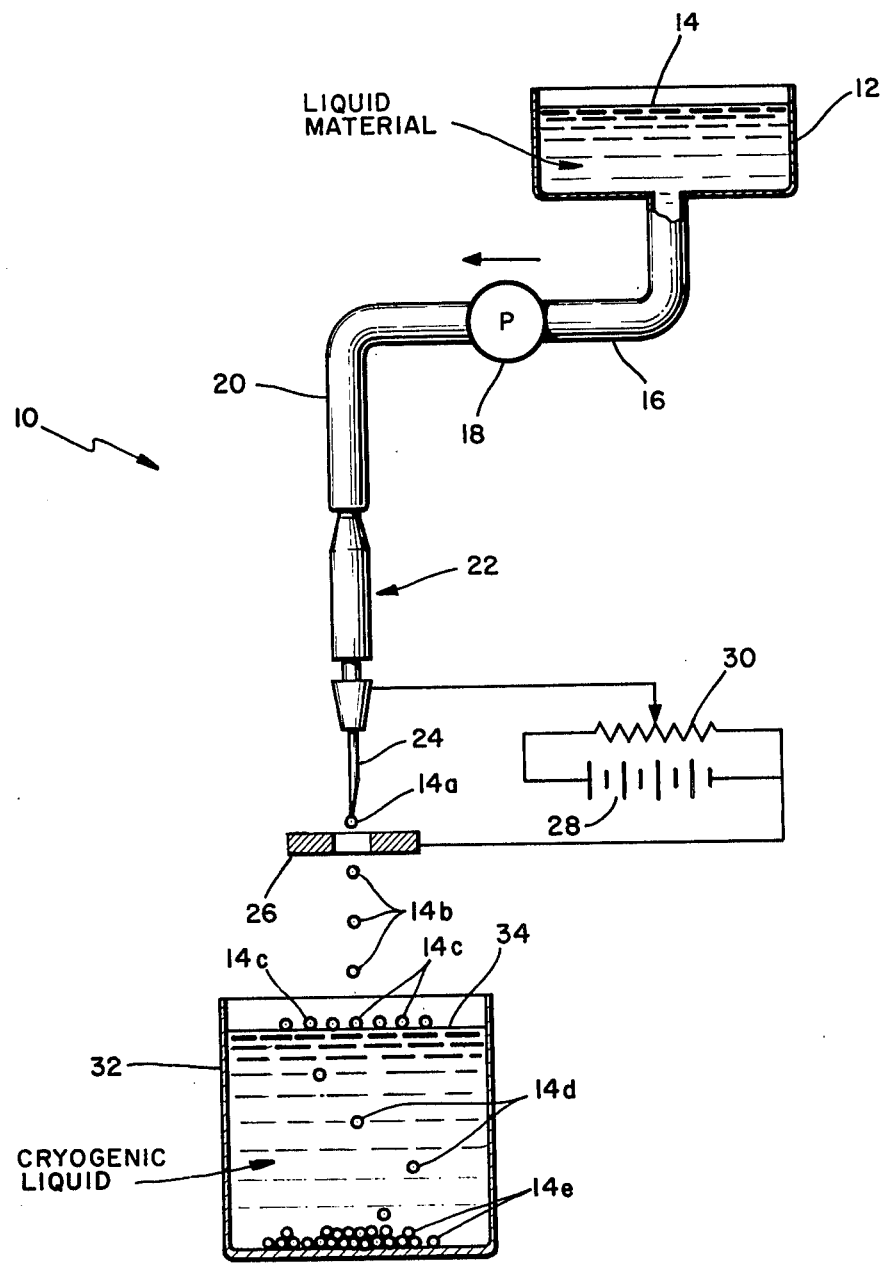

METHOD OF FREEZING LIQUID MATERIAL IN WHICH AGGLOMERATION IS INHIBITED

BACKGROUND OF THE INVENTION

1. Field of the Invention

This invention relates generally to the freezing of liquid material, and pertains more specifically to a method which separates the material into drops and inhibits the agglomeration of the drops during the time they are being cooled on the surface of a cryogenic liquid.

2. Description of the Prior Art

It is often useful to preserve material by cooling the material to temperatures below −50° C for long-term storage. Biological material, such as blood and semen, have presented special problems because of their propensity to agglomerate or coalesce. While most types of biological material can be cooled by a number of cooling methods, the placing of drops of the biological material directly on the surface of a cryogenic liquid, such as liquid nitrogen, has frequently been employed. In this process, the warm drops of material vaporize the cryogenic liquid as they cool, the drops remaining afloat until the cooling is complete, and then the resulting frozen pellets sink below the surface of the cryogenic liquid. The frozen pellets are then stored until needed at which time they can be warmed so as to be in condition for their intended use. This procedure for preserving blood was reported in the Proceedings of the Society of Experimental Biology and Medicine, Volume 90, pages 587–589 by H. T. Meryman and E. Kafig who have found that " . . . by spraying blood in very small droplets (0.45 to 0.9mm in diameter) onto the surface of liquid nitrogen, where they floated momentarily before they sank, and then rewarming the frozen pellets by sprinkling them into plasma or physiological saline at 40° C," they could get 85 to 90% recovery of the blood cells.

In 1960, however, A. P. Rinfret and G. F. Doebbler developed an apparatus utilizing the method of freezing blood that had been reported by Meryman and Kafig. This apparatus sprayed droplets of blood (0.25 to 2.0mm in diameter) onto a moving surface of liquid nitrogen, which permitted a larger scale freezing of blood. Also, the apparatus reduced the tendency of the freezing droplets to coalesce or agglomerate while cooling. The tendency to coalesce or agglomerate has been a common disadvantage as far as this type of cooling method is concerned. If no provisions are made to eliminate the tendency, large irregular clumps of frozen material are formed which do not cool and warm consistently. The problems of freezing and thawing blood, as well as the details of this process, are described in U.S. Pat. No. 3,228,838 granted Jan. 11, 1966, to Rinfret et al. for "Preservation of Biological Substances." The process and the problems associated with the freezing of blood are also lucidly dealt with in an article titled "Observations on the Freezing and Thawing of Blood in Droplet Form" authored by A. P. Rinfret and G. F. Doebbler which appears in the journal Biodynamica, Vol. 8, No. 165 (Nov., 1960), pages 181–193.

In 1971, the need arose to freeze even larger drops (4 to 5mm in diameter) of biological material on the surface of liquid nitrogen, more specifically porcine semen. Inasmuch as these larger drops require a longer period of time to freeze than the smaller drops that have been alluded to above, the coalescing or agglomerating problem became more severe. Concomitantly, the desirability of developing a simpler method of assuring that the drops of material are maintained separate from each other as they froze became more pronounced.

SUMMARY OF THE INVENTION

Accordingly, an important object of the present invention is to minimize coalescence or agglomeration in the freezing of liquid material.

Another object is to provide a method that minimizes agglomeration without adversely affecting the physical qualities of the material being frozen. A specific aim of my invention is to provide a method for preserving various types of biological material, which are especially vulnerable to agglomeration, without unduly damaging the cells constituting such material, either during the freezing or later thawing thereof. In this regard, it is extremely desirable, if not mandatory, to assure that the thawed product will be of virtually the same quality as it was prior to freezing. Inasmuch as heat, even if just at ambient or room temperature, is utilized in thawing the frozen biological material, it will be appreciated that if the frozen product is not of uniform size, which is the case when agglomeration has occurred, then portions of the material will be thawed more slowly than other portions, the greater or more prolonged heat proving, in most cases, to be deleterious to cell life where the material is of a biological nature. See the Biodynamica article hereinbefore mentioned which goes into considerable detail regarding the agglomeration problems associated with problems of preserving blood by freezing.

Still another object is to provide for the freezing of liquid material in a manner such that only the correct amount of material need be thawed, thereby obviating the waste that has previously occurred. This is particularly advantageous where the material is a biological material, for it is within the contemplation of the invention to break up or separate the biological material into small drops of uniform size and then freeze the drops into pellets that are also of uniform size. Thus, when the frozen pellets are to be used at some subsequent date, a specific number of pellets will always produce a given amount of thawed material, either on a volumetric or weight basis, it being unnecessary to thaw any more than is needed.

A specific object is to provide a method of preserving biological material that is both inexpensive and simple, requiring only low cost apparatus and no particular expertise on the part of the technician or operator.

Yet another object is to provide a method that is quite versatile, being suitable for large scale production, or in the alternative, the preservation of only small quantities which is frequently an advantage when the substance is a biological material. As far as the latter is concerned, when the material is biological, after first being separated into individual drops, it can be permitted to fall gravitationally into a test tube containing the cryogenic liquid and the test tube, after receiving a predetermined number of drops, can be stored without transferring the drops to a different container. On the other hand, the vessel or receptacle containing the cryogenic liquid therein can be quite large and a sizable number of drops of the material can be frozen, the entire collection of resulting pellets then being stored or, if desired, subdivided into prepredetermined lesser quantities. Consequently, one utilizing the teachings of my invention is provided with a complete choice as to the handling of the material, both during its freezing and during the subsequent thawing thereof.

Briefly, my invention envisages the separation of a quantity of liquid material into successive drops, each of which has an electric charge of one polarity applied thereto. The charged drops are permitted to fall gravitationally at a controlled rate, one after the other, into a vessel containing the cryogenic liquid. During the time each drop floats on the surface of the cryogenic liquid, the electric charges on the floating drops produce repulsive forces which keep the drops from touching and sticking together. This is in accordance with Coulomb's Law, for this states that the force of repulsion (or attraction) between two charges of electricity is proportional to the square of the distance between them. The force between like charges, as in this instance, produces a repulsion that is effectively made use of to reduce the objectionable agglomeration that has heretofore been experienced. In this regard, when a drop cools to the temperature of the cryogenic liquid, it then sinks as an individual pellet to the bottom of the liquid refrigerant. For all intents and purposes, owing to the fact that the drops are forced apart, each individual drop produces an individual frozen pellet. Since the pellets are solid, they do not coalesce, and the agglomerating effect which has heretofore occurred is for all intents and purposes eliminated. Because of this, the frozen pellets can be readily handled and can be later readily thawed. Because of their uniformity of size, no more heat or warmth than is necessary to thaw a given pellet need be employed and an exceptionally high cell recovery is assured for biological substances. Where a large number of pellets are to be thawed, which is more likely to be the case where non-biological material has been frozen, there can be a worthwhile saving in energy due to the uniformity of pellet size.

BRIEF DESCRIPTION OF THE DRAWING

The single FIGURE that has been presented is diagrammatically illustrative of apparatus that can be employed in carrying out my method.

DESCRIPTION OF THE PREFERRED EMBODIMENT

Apparatus suitable for practicing my method has been denoted generally by the reference numeral 10. The apparatus 10 includes a vessel 12 in which is contained the liquid material to be frozen, for example a biological substance such as blood or semen, which material has been indicated by the reference numeral 14. The vessel 12 has an outlet or opening in its bottom to which is connected a tube 16 leading to a variable speed pump 18. The discharge side of the pump 18 has a tube 20, preferably of plastic, extending therefrom to a metal hypodermic device 22 having a tubular needle 24. Concentrically disposed beneath the needle 24 is a metal ring 26.

The hypodermic needle 24 constitutes one electrode for inducing electric charges on the liquid material 14 after it has been separated into individual drops, and the ring 26 constitutes a second charging electrode. In order to develop an electric field of the proper strength, an appropriate electrical potential is impressed on the charging electrodes 24, 26 through the agency of an adjustable high voltage direct current potential source 28, shown for the sake of simplicity in the drawing as merely a battery, having a potentiometer 30 associated therewith. As the description progresses, it will become apparent that the specific voltage to be applied to the electrodes 24, 26 in order to develop the proper electric field strength will depend upon various factors, such as the dielectric characteristics of the material 14, the size of drops into which the material is separated and the delivery rate of the drops from the hypodermic needle 24 to a receptacle or vessel 32 in which is contained the cryogenic liquid 34, more specifically liquid nitrogen, which is used to freeze the drops.

Since the invention contemplates the production of various sizes of drops, depending largely on the type of material 14, where the drop size is quite small, the orifice in the needle 24 must also be quite small. Since a properly controlled delivery rate from the hypodermic needle 24 to the receptacle 32 is important, it is planned that the needle 24 be suitably vibrated, for instance ultrasoncially, to assist the pump 18 in breaking up the stream of liquid into very small droplets.

It has already been mentioned that the specific potential applied between the electrodes 24 and 26 is susceptible to variation, depending upon such factors as the size of drop, the rate of drop delivery, and the type of material 14. Likewise, the physical dimensions of the apparatus 10 are influenced by such variables. As an example of what has been used, it can be stated that the metal ring 26, this being one of the charging electrodes, can have an internal diameter on the order of 1.0cm whose axis coincides with the axis of the hypodermic needle 24. The ring 26 should be located relatively close to the needle 24, approximately 5mm from the lower end of the needle 24 having been found satisfactory.

Consequently, as a drop 14a forms at the end of the needle 24, an electric charge is induced on the surface of the drop 14a by the electric field established between the needle 24 and the ring 26. As the drop 14a falls gravitationally from the tip of the needle 24, the drop retains a net electrostatic charge of one polarity or the other depending on the terminal connections of the high voltage source 28 to the electrodes 24, 26.

It will be appreciated that the various drops 14a, which leave the needle 24 in sequence or succession, each carry the same amount of electric charge which is determined by the particular setting to the potentiometer 30. The sequence of drops delivered from the needle 24 has been indicated by the reference numeral 14b and their delivery rate is controlled by the speed of the pump 18, assisted (if need be) by a vibrator (not shown). The various drops 14b fall through the center of the ring 26 without difficulty and impinge onto the surface of the cryogenic liquid 34, more specifically the liquid nitrogen which has previously been mentioned.

Each drop floats on the surface of the liquid nitrogen 34 and these floating drops have been labled 14c. It must be borne in mind that during the time that the drops 14c float on the surface of the liquid 34, the like charges on each drop 14c provide repulsive forces in accordance with Coulomb's Law, the repelling forces keeping the drops 14c from touching and becoming coalesced or agglomerated.

Each drop 14c may remain on the surface of the liquid 34 for as long as 30 seconds, depending upon the size of drop and the time needed to freeze it. Since the drops 14c, when of larger size, have more mass, they necessarily require a higher charging voltage in order to assure their separation during the cooling time. The best charging potentional can readily be determined by noting the result as far as the drops 14c are concerned. In this regard, it is intended that the drops 14c dance around but not bounce upwardly from the surface of the liquid 34. Consequently, the voltage supplied by the source 28 can be adjusted via the potentiometer 30 so as to maintain the various drops 14c separated, yet not cause any undue bouncing.

When the drops 14c solidify, they sink as pellets 14d and are connected at the bottom of the receptacle 32, the collected pellets being identified by the reference numeral 14e. The pellets 14d may very well retain their charge after becoming solid but even if retained upon reaching the bottom, no difficulty is caused. As a matter of fact, the retention of even a portion of the initial charge, as far as the pellets 14e are concerned, can be an aid to the facile handling of the frozen pellets. It should be remembered that the charge impressed on the drops 14a, 14b, and 14c are all of one polarity, being either positive or negative, and any remaining charge on the pellets 14d and 14e will be of the same polarity or sign. It has already been explained that like charges, under Coulomb's Law, produce a repelling effect, and this tends to simplify the collection procedure.

Generally speaking, the results to be realized from a practicing of my invention dictate that the optimum charging voltage should be increased as the size of drop 14a increases and should also be increased with an increase in drop delivery rate. This generalization can be explained in three ways:

(1) Larger drops, which spend more time on the surface of the cryogenic liquid 34 before sinking, coupled with a higher delivery rate thereof from the hypodermic needle 24, increases the number of floating drops 14c per unit area on the surface of the liquid 34. This increases the chance of a collision between the drops 14c and requires a correspondingly greater voltage between the electrodes 24, 26 which is needed in order to increase the electric field strength sufficiently to induce or apply a greater charge to each drop 14a in order to produce a repulsive force sufficiently large to keep the drops 14c separated.

(2) The larger drops have a greater mass, requiring a greater repelling force, and again requiring a greater charging voltage in order to repel the drops 14c during the random motion that they exhibit during their cooling on the surface of the liquid 34.

(3) The larger dimensions of the larger drops mean that they can touch and coalesce at greater center-to-center distances, again requiring a greater force and a correspondingly greater charging voltage in order to keep them separated.

Consequently, it should be recognized that the potentiometer 30 should be adjusted so as to impress virtually the full potential of the source 28, say 1500 volts or even more, when the drop size is on the order of 1.0cm, and 500 volts or less when the drop size is on the order of 0.8mm.

Since my invention effectively inhibits agglomeration, as is believed evident from the foregoing description, it will find especial utility in the preservation of biological substances, particularly blood and semen, as hereinbefore mentioned.

I claim:

1. A method of freezing a quantity of liquid material comprising the steps of separating said quantity of material into individual drops, applying an electric charge of one polarity to said drops, and freezing said drops while still charged.

2. The method of claim 1 in which said material is a biological substance to be preserved.

3. The method of claim 2 in which the biological substance is blood or semen.

4. The method of claim 1 in which said charging and freezing steps are performed at spaced locations.

5. The method of claim 4 in which said charging location is at one elevation and said freezing location is at a lower elevation therebeneath.

6. The method of claim 5 in which said charging step is performed with an electric field and said freezing step is performed with a cryogenic liquid so as to freeze said drops into solid pellets.

7. The method of claim 6 in which said drops are delivered to said cryogenic liquid at a controlled rate.

8. The method of claim 7 in which said drops are permitted to fall gravitationally from said one elevation to said lower elevation at said controlled rate.

9. The method of claim 8 in which said rate is selected in accordance with the size of said drops.

10. The method of claim 9 in which the strength of the electric field utilized in charging said drops is increased for larger size drops when being delivered at given rate.

11. The method of claim 9 in which the strength of the electric field utilized in charging said drops is increased for a greater delivery rate when the size of drop remains the same.

12. The method of claim 9 in which the strength of the electric field utilized in charging said drops is increased as the drop size and delivery rate is increased.

13. The method of claim 9 in which the strength of the electric field utilized in charging said drops is increased when either the size of drops or their delivery rate is increased.

14. The method of claim 9 in which the strength of the electric field utilized in charging said drops is selected so that the charges applied to the drops maintain the charged drops, when floating on the surface of the cryogenic liquid, separated and which does not cause the floating drops to bounce upwardly from the surface of the cryogenic liquid.

* * * * *